(12) United States Patent
Journey et al.

(10) Patent No.: US 11,160,631 B2
(45) Date of Patent: Nov. 2, 2021

(54) INSTRUMENTS AND METHODS FOR SURGICAL SIZING AND MARKING

(71) Applicants: Michelle L. Journey, Carlsbad, CA (US); Jason Shih, Yorba Linda, CA (US); Sean Caffey, Hawthorne, CA (US); Gregory Harbers, Valencia, CA (US)

(72) Inventors: Michelle L. Journey, Carlsbad, CA (US); Jason Shih, Yorba Linda, CA (US); Sean Caffey, Hawthorne, CA (US); Gregory Harbers, Valencia, CA (US)

(73) Assignee: MINIPUMPS, LLC, Pasadena, CA (US)

(*) Notice: Subject to any disclaimer, the term of this patent is extended or adjusted under 35 U.S.C. 154(b) by 437 days.

(21) Appl. No.: 15/951,800

(22) Filed: Apr. 12, 2018

(65) Prior Publication Data

US 2018/0289442 A1 Oct. 11, 2018

Related U.S. Application Data

(63) Continuation of application No. 13/646,124, filed on Oct. 5, 2012, now abandoned.
(Continued)

(51) Int. Cl.
*A61B 90/00* (2016.01)
*A61B 17/02* (2006.01)
(Continued)

(52) U.S. Cl.
CPC .......... *A61B 90/06* (2016.02); *A61B 17/0231* (2013.01); *A61B 90/39* (2016.02);
(Continued)

(58) Field of Classification Search
CPC ..... A61B 17/0231; A61B 19/46; A61B 19/54; A61B 2019/00716; A61B 2019/5408; A61F 9/0019; A61F 9/0136; A61F 2240/005
See application file for complete search history.

(56) References Cited

U.S. PATENT DOCUMENTS

| 1,433,340 A | 10/1922 | Samuel et al. |
| 1,561,116 A | 11/1925 | Silliman et al. |

(Continued)

FOREIGN PATENT DOCUMENTS

| CH | 554239 | 9/1974 |
| EP | 10693 | 5/1980 |

(Continued)

OTHER PUBLICATIONS

International Search Report and Written Opinion for International application No. PCT2012058944 dated Apr. 9, 2013.
(Continued)

*Primary Examiner* — Nathan R Price
*Assistant Examiner* — Anh Bui
(74) *Attorney, Agent, or Firm* — Morgan, Lewis & Bockius LLP (57) ABSTRACT

A surgical sizer for creating a tissue pocket for an implantable medical device may include a replica of the device and a (preferably ergonomic) handle portion, optionally with marking features that facilitate marking the tissue for precise implant placement and alignment.

28 Claims, 6 Drawing Sheets

Related U.S. Application Data (60) Provisional application No. 61/543,519, filed on Oct. 5, 2011.

(51) Int. Cl.
  *B33Y 80/00* (2015.01)
  *A61F 9/00* (2006.01)
  *A61F 9/013* (2006.01)
  *A61B 17/00* (2006.01)

(52) U.S. Cl.
  CPC ............... *A61B 2017/00716* (2013.01); *A61B 2090/3908* (2016.02); *A61B 2090/3937* (2016.02); *A61F 9/0017* (2013.01); *A61F 9/0136* (2013.01); *A61F 2240/005* (2013.01); *B33Y 80/00* (2014.12)

(56) References Cited

U.S. PATENT DOCUMENTS

| | | |
|---|---|---|
| 2,555,076 A | 5/1951 | Crossley et al. |
| 4,036,230 A | 7/1977 | Waldock |
| 4,375,218 A | 3/1983 | DiGeronimo |
| 4,406,285 A | 9/1983 | Villasenor et al. |
| 4,705,035 A | 11/1987 | Givens |
| 4,739,761 A | 4/1988 | Grandon |
| 4,844,065 A | 7/1989 | Faulkner |
| D304,078 S | 10/1989 | Jensen |
| 4,880,017 A | 11/1989 | Soll |
| 4,917,677 A | 4/1990 | McCarthy |
| 5,006,123 A * | 4/1991 | Soil ........................ A61F 9/007 33/512 |
| 5,007,913 A | 4/1991 | Dulebohn |
| 5,021,057 A | 6/1991 | Byrne |
| 5,484,447 A | 1/1996 | Waldock et al. |
| 5,697,945 A | 12/1997 | Kritzinger et al. |
| 5,752,967 A | 5/1998 | Kritzinger et al. |
| 5,797,954 A | 8/1998 | Shaffer et al. |
| 5,893,853 A | 4/1999 | Arnold |
| 6,113,606 A | 9/2000 | Dykes |
| 6,171,324 B1 | 1/2001 | Cote et al. |
| D439,976 S | 4/2001 | Cote |
| 6,248,123 B1 | 6/2001 | McDonald |
| 6,251,090 B1 * | 6/2001 | Avery ................... A61F 9/0017 604/294 |
| 6,280,449 B1 * | 8/2001 | Blake ................... A61F 2/1664 606/107 |
| 6,447,528 B2 | 1/2002 | Paraschac |
| 6,554,829 B2 | 4/2003 | Schulze |
| 6,786,926 B2 | 9/2004 | Peyman |
| 7,160,297 B2 | 1/2007 | Nesbitt |
| 7,972,348 B1 * | 7/2011 | Anderson ............. A61F 9/0136 606/166 |
| 2002/0133168 A1 | 9/2002 | Smedley et al. |
| 2005/0125013 A1 | 6/2005 | Kessler |
| 2005/0203554 A1 * | 9/2005 | Dykes ................... A61B 90/39 606/166 |
| 2006/0258994 A1 | 11/2006 | Avery |
| 2008/0081952 A1 | 4/2008 | Josephberg |
| 2008/0255578 A1 | 10/2008 | Neusidl |
| 2010/0057094 A1 | 3/2010 | Akahoshi |
| 2010/0106202 A1 | 4/2010 | Gannoe et al. |
| 2010/0137780 A1 | 6/2010 | Singh et al. |
| 2010/0331770 A1 | 6/2010 | Lee et al. |
| 2011/0112546 A1 | 5/2011 | Juan et al. |

FOREIGN PATENT DOCUMENTS

| | | |
|---|---|---|
| FR | 2906997 | 4/2008 |
| FR | 29129011 | 8/2008 |
| NL | 1005694 C2 | 10/1998 |
| WO | 9636377 | 11/1996 |
| WO | 1999030656 | 6/1999 |
| WO | 2008085966 | 7/2008 |
| WO | 20100031691 | 1/2010 |
| WO | 2001087200 | 11/2011 |

OTHER PUBLICATIONS

International Search Report and Written Opinion for International Application No. PCT2012021540 dated Jun. 28, 2012 12 pages.

* cited by examiner

INSTRUMENTS AND METHODS FOR SURGICAL SIZING AND MARKING

CROSS-REFERENCE TO RELATED APPLICATION

The present application is a continuation of U.S. patent application Ser. No. 13/646,124, filed on Oct. 5, 2012, which claims priority to and the benefit of U.S. Provisional Patent Application No. 61/543,519, filed on Oct. 5, 2011, the entire disclosure of each of which is hereby incorporated herein by reference.

TECHNICAL FIELD

This invention relates to surgical sizing instruments for creating appropriately sized tissue pockets prior to insertion of medical implants. In various embodiments, the invention also relates to instruments and tools that facilitate marking the tissue to aid proper positioning and alignment of the implant.

BACKGROUND

Most surgeries conducted to implant medical devices (such as, e.g., pacemakers) include a procedural step in which the surgeon fashions a "pocket" in the tissue in which the medical device is to be implanted. The implementation of this step varies by surgeon, resulting in varying sizes of the pockets created. While this variability is generally not an issue of great importance in a highly vascular region of the body that quickly heals, it can be problematic in delicate organs, such as, e.g., the eye. Medical eye implants include, for example, Ahmed glaucoma valves, which are used to drain aqueous humor out of the eye to treat certain types of glaucoma (an eye disease due, typically, to increased intraocular pressure, which generally results in damage to the optic nerve), and ophthalmic miniature drug-pump devices. Current procedures for insertion of such medical devices into the eye rely on the surgeon's skill to create an incision and insert the medical device without any prior sizing of the pocket. This process can lead to unwanted tearing of tissue and rupture of blood vessels, which may delay patient recovery, as well as to possible damage to the delicate external components of the medical device, which can compromise its functionality. Furthermore, without a properly sized pocket, it may be difficult to precisely place and anchor the medical device in the tissue. Accordingly, there is a need for instruments that facilitate forming an accurately shaped and sized pocket for medical-device implantation in the tissue and/or that aid in the proper positioning of an implant within the pocket.

SUMMARY

The present invention provides surgical sizing and/or marking instruments that aid surgeons in the implantation of medical devices. In various embodiments, the surgical sizing instrument ("surgical sizer") includes or consists of a replica of the actual medical device to be implanted (possibly scaled in size) that is fixedly attached to an ergonomic handle. A replica of a medical device, as defined herein, is a structure that is substantially similar in its exterior three-dimensional shape to the medical device. However, the replica may omit certain structural details, such as refill ports or minor surface structures, that do not significantly affect the shape of the exterior surface and/or whose omission is not clinically relevant to the body's ability to accommodate the actual implantable device in a pocket formed by the replica. Such replicas are considered "substantially similar in shape" to the implantable medical device. More generally, the term "substantially" or "approximately" means ±10%, and in some embodiments, ±5%.

In contrast to conventional sizers, which serve to measure the size of a tissue pocket or orifice by incrementally altering movable elements until they correspond to the dimensions of the pocket or orifice, a sizer in accordance herewith facilitates creating an appropriately sized pocket for the implantable medical device and simultaneously verifying insertion feasibility prior to actual insertion of the device. Since the medical-device replica is fixedly attached to the handle, the surgeon cannot lose the device, as might be the case if the surgeon were to size the pocket by using an introducer to grip the device.

In various embodiments, the surgical sizer also includes features or tools that provide the surgeon with the ability to accurately mark relevant anatomical landmarks during sizing. Alternatively, in some embodiments, surgical sizers and markers are provided as two separate instruments, each including a handle and, fixedly attached thereto, either a replica of the implant or a marking portion.

While surgical sizers/markers in accordance herewith can be used for many types of implants (e.g., drug pumps, pacemakers, other neural stimulators), embodiments of the invention can be particularly helpful in the insertion process of implants that are delicate in nature (e.g., microelectronic devices or infusion pumps with flexible cannulas) and/or require precise placement and markers for possible anchoring techniques. Accordingly, one area where the use of surgical sizers/markers in accordance herewith is particularly beneficial is that of ophthalmic surgery.

In one aspect, the present invention provides an instrument facilitating surgical implantation of an implantable device. The instrument includes a pocket-forming portion substantially shaped like the implantable device, and a grippable handle portion extending away from and joined to the pocket-forming portion. By "joined" is meant forming a unitary structure; accordingly, two separate structures permanently fixedly attached to form a single structure, or a single structure having distinct portions (e.g., pocket-forming and handle portions), are joined as that term is used herein. The pocket-forming portion may include a positively scaled (e.g., slightly larger) replica of the implantable device. Further, it may have a curvature that is complementary to an internal anatomical contour (e.g., an ocular orbit). The handle portion has a length adequate to facilitate external manual retention of the instrument with the pocket-forming portion disposed within an internal anatomical site.

In some embodiments, the instrument includes or consisting essentially of a polymer material and/or a metal (such as, e.g., stainless steel, titanium, niobium, nickel titanium, or an alloy). The material is preferably biocompatible. In some embodiments (particularly in embodiments of instruments intended for repeated use), an autoclave-safe metal is used. In other embodiments (particularly in embodiments of instruments intended for one-time use), an autoclave-degradable polymer is used. The surface of the instrument (or a surface portion) may be coated with parylene.

The handle portion is in some embodiments planar and in others non-planar. It may be joined to the pocket-forming portion in a planar fashion. At an end opposite the pocket-forming portion, the handle portion may include a cut-out that is anatomically compatible with a human thumb. The cut-out may be textured, and may form, e.g., a circle, a slot, or a hook shape.

In certain embodiments, the handle portion includes, in a distal portion thereof, one or more markings, such as, e.g., two circular indentations proximate a terminus of the pocket-forming portion, or a distance marking at 8 mm from the from a terminus of the pocket-forming portion and, optionally, distance markings at 3.5 mm and 4 mm from the distance marking at 8 mm. In some embodiments, the handle portion includes a slot proximate a terminus of the pocket-forming portion. The ends of the slot may be semicircular in shape. The instrument may further include a marking tool with a tip (e.g., a felt tip or a non-piercing protrusion) suspended above and sized to fit through the slot; the marking tool is configured to mark tissue when engaged.

In a further aspect, the invention provides an instrument facilitating marking tissue at an implantation site of an implantable device. The instrument includes a marking portion having one or more features for marking the tissue, and a handle portion joined to the marking portion (e.g., fixedly attached thereto or forming a single structure with the marking portion, as defined above). The handle portion may be planar or non-planar, have one or more textured regions, and/or include a cut-out at a proximal end, and may generally have features and characteristics like the handle of a surgical sizer as described above. In some embodiments, the marking portion is joined to the handle portion at an angle; in other embodiments, it is joined to the handle portion in a planar fashion. The marking portion may include a cut-out for alignment with an anatomical landmark. Further, it may have, at an underside, one or more non-piercing protrusions for marking tissue. The marking portion may also include distance markings, circular indentations, or a slot (and optionally, an integrated marking tool with a tip above the slot) as described above with respect to marking portions in a surgical sizer. The marking instrument may be fabricated from (preferably biocompatible) metals and/or polymers, and may be autoclave-safe or autoclave-degradable, depending on the intended use. The surface of the marking instrument (or a surface portion) may be coated with parylene.

In another aspect, the invention may be directed to a method of fabricating an instrument facilitating surgical implantation of an implantable device. The method includes fabricating a structure including a pocket-forming portion substantially shaped like the implantable device and, joined thereto, a handle portion from a metal and/or a polymer (e.g., by injection molding or stereolithography), depositing a first polymer layer on the structure, and then depositing a second polymer layer on an underside of the structure. The first polymer layer may be hydrophobic and, e.g., include or consist essentially of parylene, and the second polymer layer may include silicone. The method may further include using a cut-out, a slot, or an indentation formed in the structure to hold the structure during the deposition steps.

In yet another aspect, the invention may be directed to a method of fabricating an instrument facilitating marking tissue at an implantation site of an implantable device. The method includes fabricating a structure including a marking portion and a handle portion joined thereto from a metal and/or a polymer (e.g., by injection molding or stereolithography), depositing a first polymer (e.g., parylene or another hydrophobic polymer) layer on the structure, and then depositing a second polymer (e.g., silicone) on an underside of the structure. The method may further include using a cut-out, a slot, or an indentation formed in the structure to hold the structure during the deposition steps.

BRIEF DESCRIPTION OF THE DRAWINGS

The foregoing will be more readily understood from the following detailed description, in particular, when taken in conjunction with the drawings, in which.

DETAILED DESCRIPTION

Figure 1:
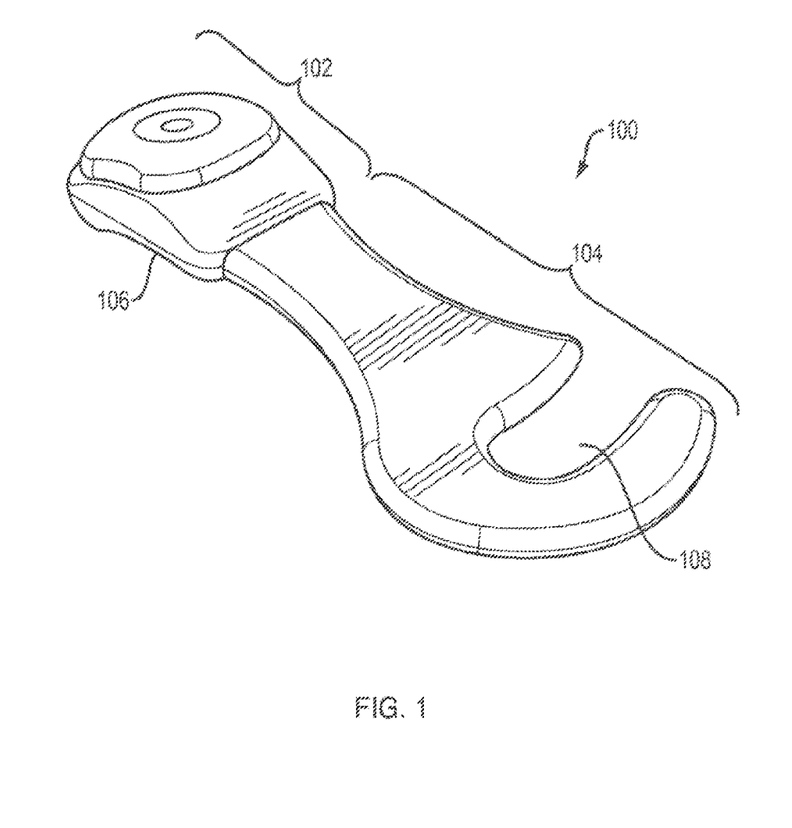
FIG. 1 is an isometric view of a planar surgical sizer in accordance with one embodiment.

FIG. 1 illustrates a representative embodiment of a surgical sizer 100 in accordance with the invention. The sizer includes a pocket-forming portion 102 and a substantially planar ergonomic handling portion 104. In the example shown, the pocket-forming portion takes the shape of a micropump device to be implanted. Certain detailed aspects of the actual micropump device, such as its refill port, need not be reproduced in the pocket-forming portion; omitting such details may serve to simplify manufacturing, and reduce the number of features that could potentially damage the tissue if not properly fabricated. Further, the pocket-forming portion may be slightly larger than the actual micropump; for example, it may be scaled to 110%. The pocket-forming portion, like the device it replicates, may be shaped to follow the contours of the relevant anatomy so as to prevent causing damage to delicate tissue. (Damage to tissue in surgery can increase healing time and cause unnecessary discomfort to the patient.) In the illustrated embodiment, the anatomical organ is the eye. Therefore, the pocket-forming portion 102 has a curved underside 106 that is complementary to the eye.

The holding end of the handling portion 104 may have a cut-out (or groove) 108 anatomically compatible with a human thumb to provide the surgeon with a gripping surface and tactile feedback during surgery. This cut-out 108 may take the form of a circular hole, an elongated slot, or other shape (e.g., a hook-shape), and have a textured grip for additional feedback. The entire proximal portion of the tool can, optionally, be textured in order to allow the surgeon to grip the tool, while keeping the distal end relatively smooth, e.g., with a coating of silicone or parylene.

Figure 2A:
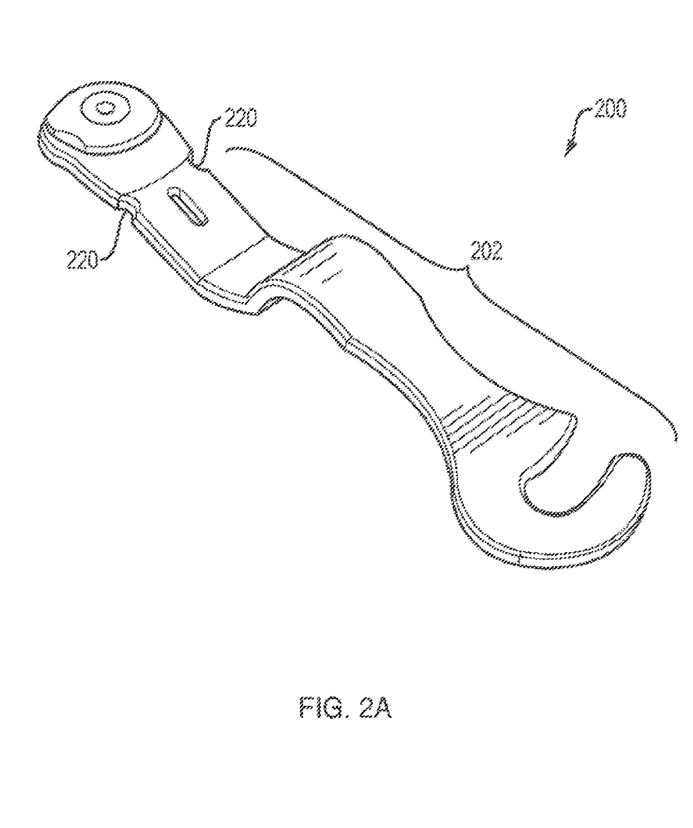
FIGS. 2A-2C are isometric, side, and top views, respectively, of a non-planar surgical sizer with marking features in accordance with one embodiment.
Figure 2B:
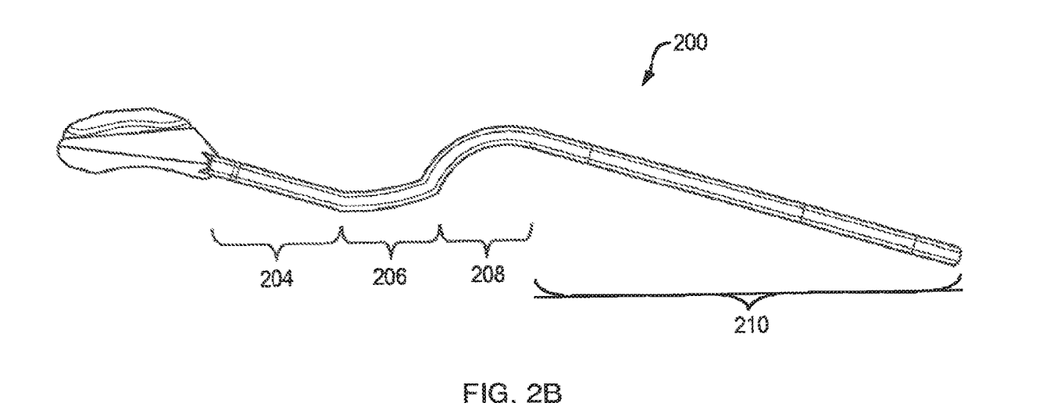
Figure 2C:
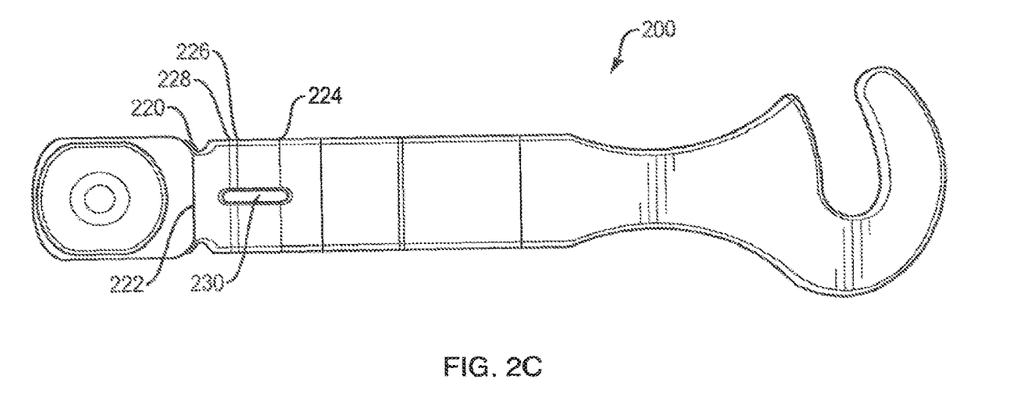

FIGS. 2A-2C illustrate another embodiment of a surgical sizer for an implant shaped similarly to the replica 102 of FIG. 1. The surgical sizer 200 shown in FIGS. 2A-2C has a handling portion 202 that is (in contrast to the handling portion 104 of the sizer 100 of FIG. 1) non-planar. Non-planar geometries may facilitate easier access to the implantation site; the precise shape and curvature of the handling portion 202 may be tailored to the particular surgical procedure, anatomical site, and access route. For example, as illustrated in FIG. 2B, the handle portion 202 may have different sections 204, 206, 208, 210 with different radii of curvature (including planar sections 204, 210 and curved sections 206, 208). In sizers used to prepare device-implantation into the eye, the radius of curvature is often greater than that of the eye in order to prevent the bottom surface of the instrument from touching the cornea during manipulation of the tool. Depending on the particular application, surgical sizers in accordance herewith may include differently curved ergonomic handling portions to aid the surgeon in placing the micropump or other device into the applicable anatomic region, e.g., the space between the dura mater and meninges, the sphenoid bone of the skull right under the left or right temporal region, or the spine adjacent to the neural root (for delivery of pain medication such as fentanyl).

The surgical sizer 200 may have various marking features at which the surgeon may opt to mark the eye with a felt-tip marker, bovie, cauterizing tool, or other comparable marking tool to identify certain locations proximate the anatomic location where an implant should be placed. For example, as shown in FIGS. 2A and 2C, the sizer 200 may have, at the distal end of the handle portion 202, two semi-circular indentations 220. These indentations 220 may correspond to the location of anchoring features, or other relevant structural features, of the implant, and may be used to determine the placement of anchoring sutures by marking the locations of the holes of suture rings of the drug pump or other implant; this may help to align the implant in a correctly sized pocket at the correct location of the eye by aligning the suture rings. The terminus 222 of the pocket-forming portion, and markings near the terminus, may aid the surgeon in realizing when the sizer 200 should not be pushed any farther in the posterior direction. Proper location of the implanted device is important to a patient's comfort and, at times, to the functionality of the device.

Figure 3A:
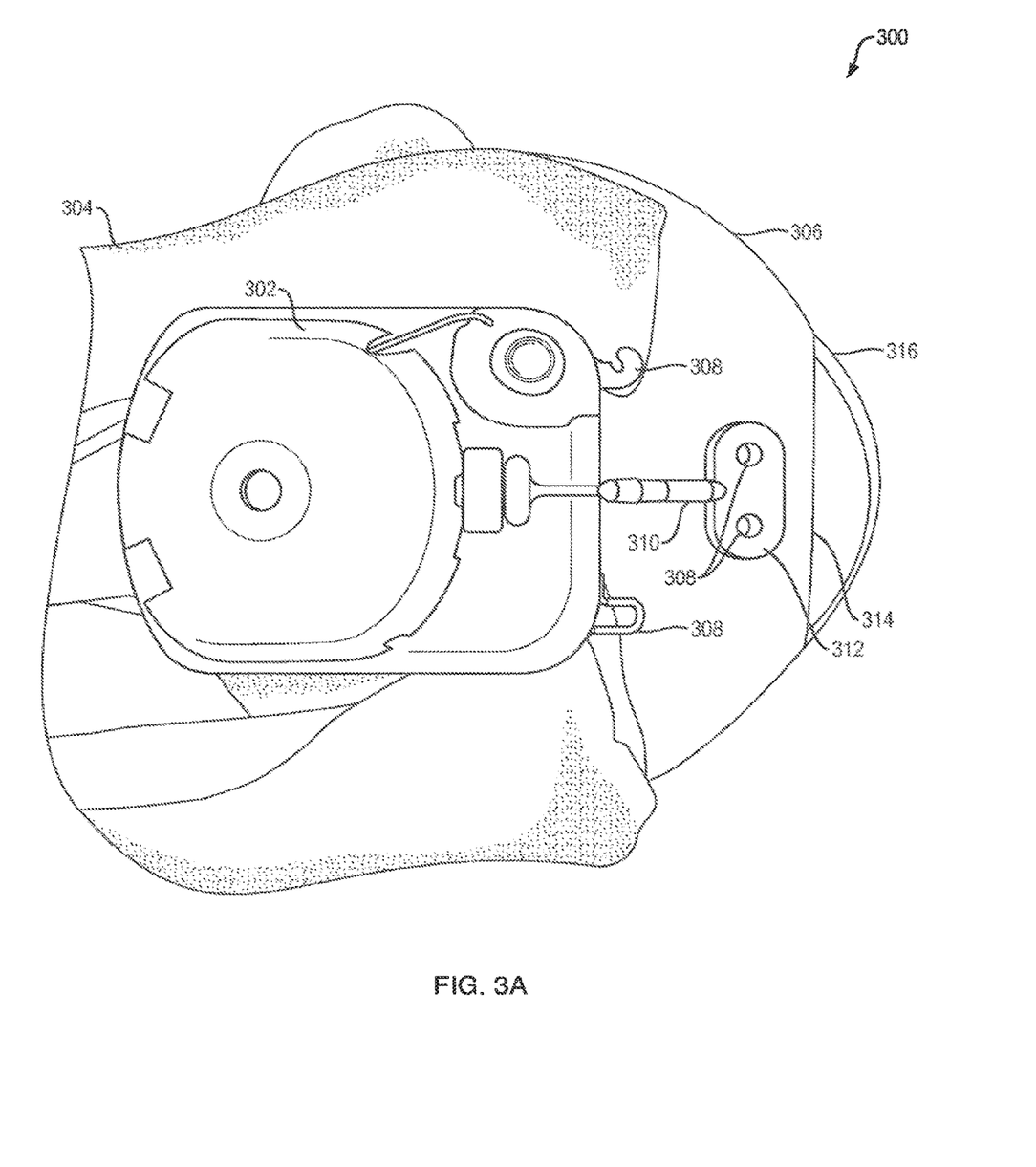
FIGS. 3A-3B are top and side views, respectively, of a drug pump device implanted into a human eye in accordance with various embodiments.
Figure 3B:
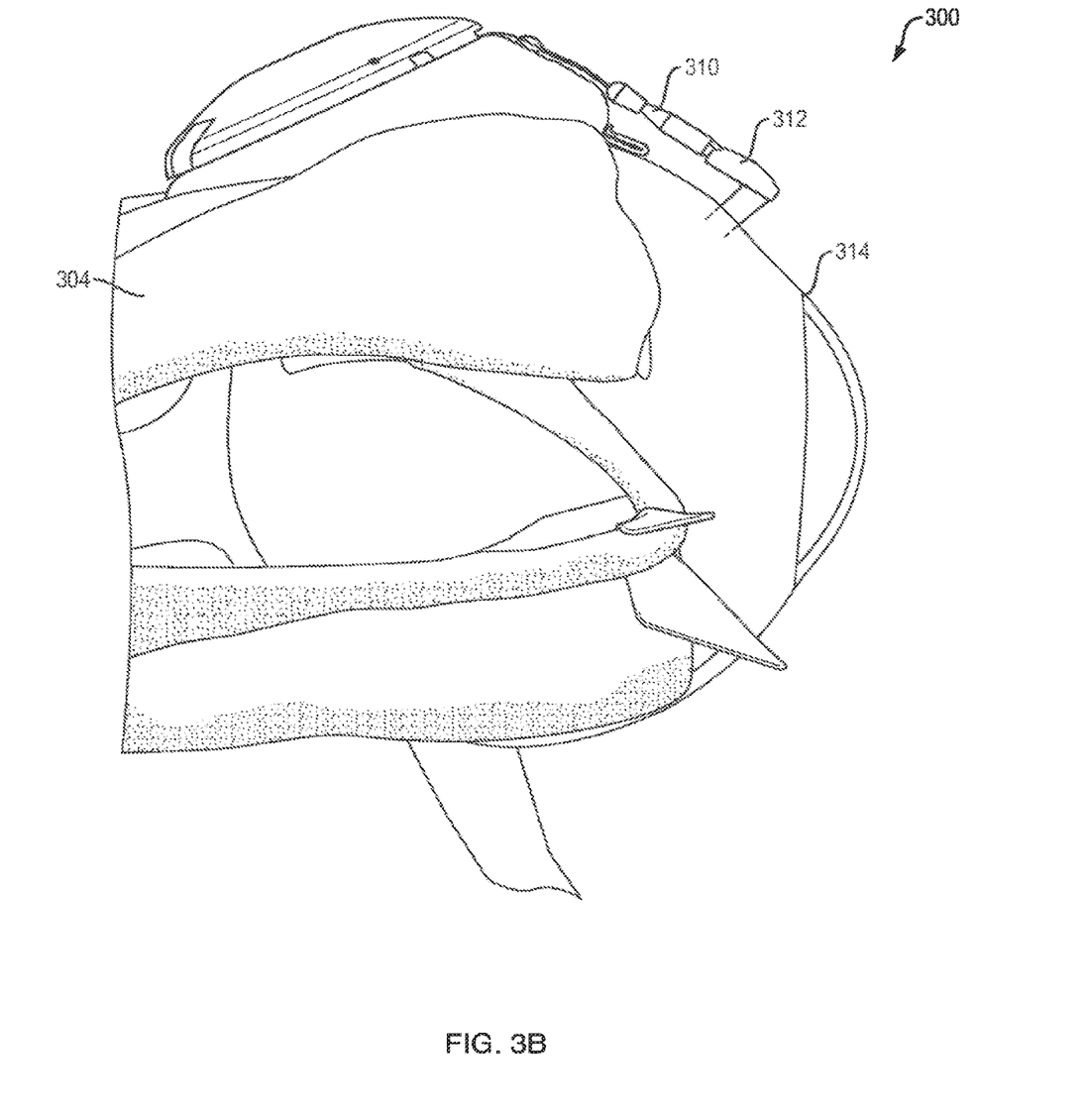

The sizer 200 shown in FIGS. 2A-2C is adapted, specifically, for implanting a drug pump device into the eye. For reference, FIGS. 3A and 3B show top and side views of a human eye 300 with a drug pump device 302 implanted. Typically, the implant 302 is placed between the rectus muscles 304 of the eye and fastened to the underlying sclera 306 with two (or more) permanent sutures through respective suture anchors 308 on the device 302. The cannula 310 of the pump device 302 may be inserted into the pars plana (a posterior flat region of the ciliary body surrounding the iris) via a suitable sutured clip 312. A small piece of donor tissue (e.g., sclera or pericardium) may be placed over the cannula 310 to avoid or limit erosion through the overlying conjunctiva.

The preferred implantation position of ophthalmic drug pumps as shown in FIGS. 3A-3B, as well as of Ahmed valves (or similar glaucoma drainage valves), is approximately 8 mm posterior to the corneal limbus 314, i.e., the border between the cornea 316 and the sclera 306. Accordingly, as shown in FIG. 2C, the sizer 200 may have, at 8 mm from the terminus 222, a distinct marking 224 (e.g., a line or grove across the handle tab 202) that aligns with the eye's limbus 314. Further, the handle portion 202 may have distinct distance markings 226, 228 at 3.5 mm and 4 mm, respectively, from the distance marking 224 at 8 mm to determine the placement of the pars plana clip 312 and cannula 310 for a normal lens and an artificial intraocular lens, respectively. The distance markings may have associated holes or slots that allow the distance to be marked on the tissue using any one of the methods mentioned above. For example, the sizer 200 of FIGS. 2A-2C includes a slot 230 with semi-circular end portions extending between the limbus marking 224 and the markings 226, 228 at 3.5 mm and 4 mm therefrom, which allows a pen or cauterizing tool, for example, to mark the desired placement of a pump cannula 310 and pars plana clip 312. Optionally, additional markings at specific distances (e.g., in millimeter increments indicative of the distance to the far edge of the pocket-forming portion) along the handle portion 202 may provide a guide to let the surgeon know when the device has reached its optimum or required depth. The markings may, generally, be tactile and/or visual in nature; for example, they may be grooves or notches perceptible by touch, or simply lines drawn onto the handle portion 202. Of course, the types and locations of markings illustrated in FIGS. 2A and 2C are exemplary only; those of skill in the art will readily be able to adapt the markings to surgical tools for a variety of other applications.

Figure 4:
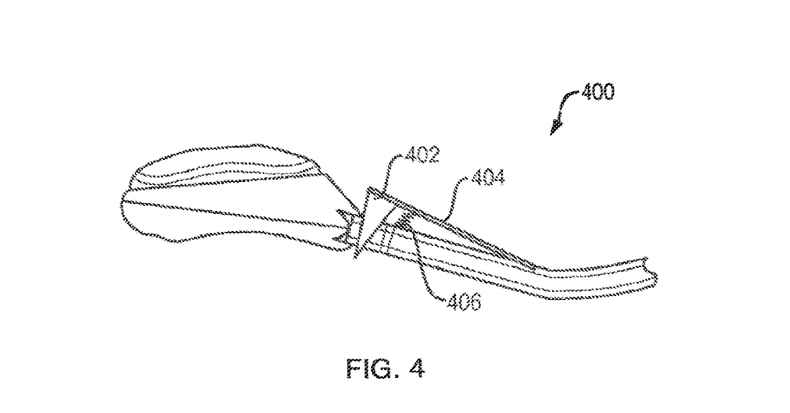
FIG. 4 is a side view of a marking portion of a surgical sizer in accordance with one embodiment.

In some embodiments, illustrated in FIG. 4, a marking tool 400, including, e.g., a felt tip 402, is integrated into the body of the surgical sizer. The tip 402 of the marking tool 400 may be disposed above and sized to fit through a marking hole in the sizer, such as the slot 230 shown in FIG. 2C, allowing the surgeon to mark the tissue by, for example, depressing or unlocking a lever 404 (e.g., held at a distance from the handle portion by means of a spring 406) to which the marking tip 402 is attached. Further, the felt tip 402 may be placed, and the sizer configured, to accommodate any curvature of the organ or anatomical surface where the implant will be located (e.g., the surface of the eye) while maintaining proper alignment, e.g., so that the felt tip 402 is perpendicular to the organ's surface when the sizer is positioned properly against the anatomical surface. Furthermore, the tip 402 may be extendible and retractable to further accommodate anatomical variation or the surgeon's preference. Following marking of the tissue, the marking tool 400 may be removed and discarded.

Figure 5A:
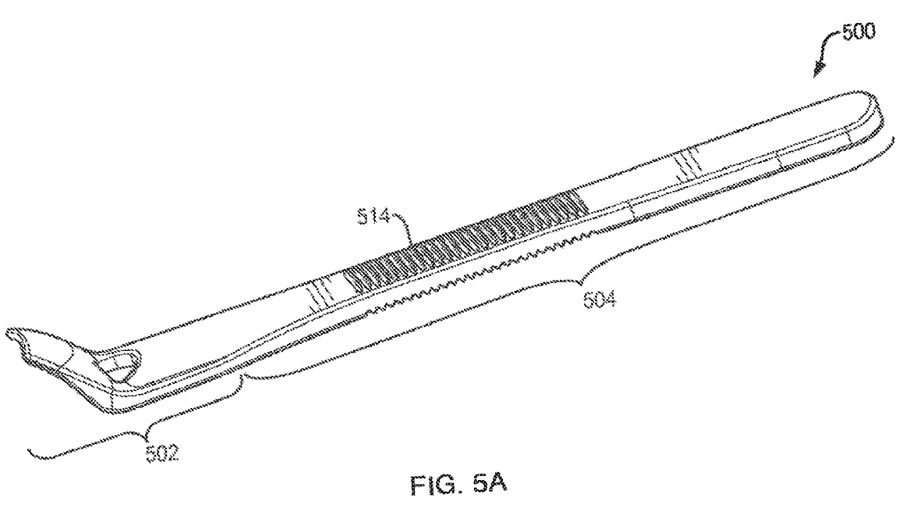
FIG. 5A is a perspective view of a surgical marking instrument with a textured handle portion in accordance with one embodiment.
Figure 5B:
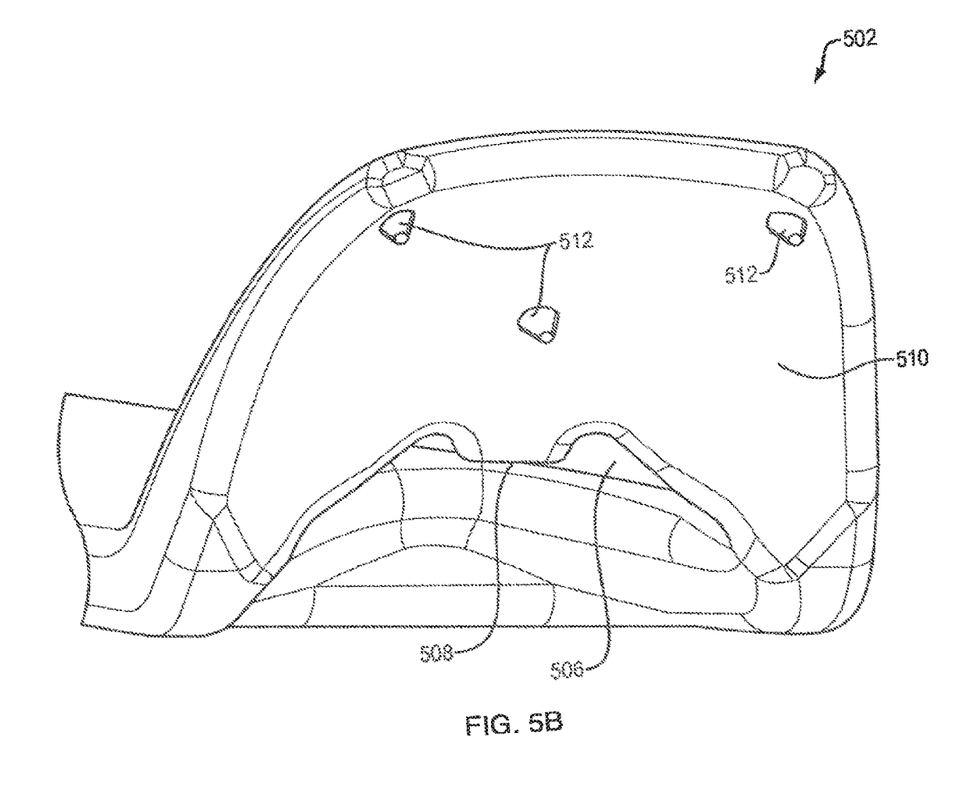
FIGS. 5B, 5C, and 5D are isometric, side, and top views, respectively, of a marking portion of the instrument of FIG. 5A.
Figure 5C:
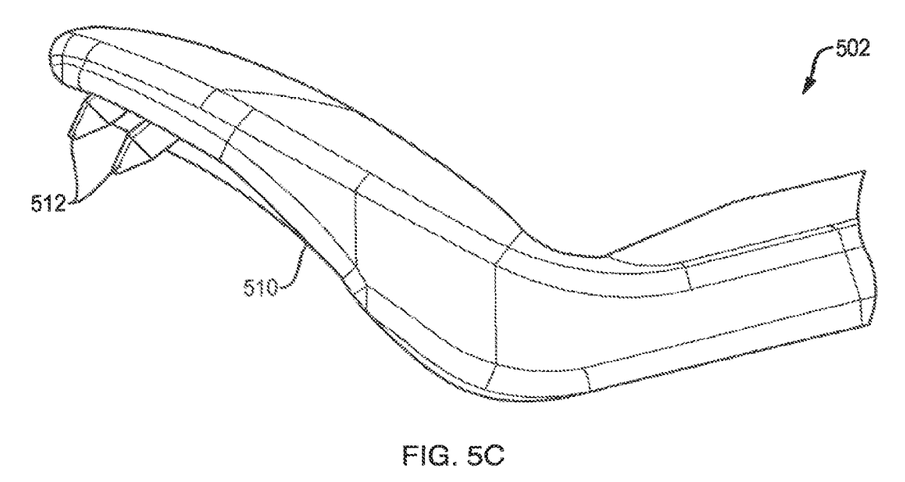
Figure 5D:
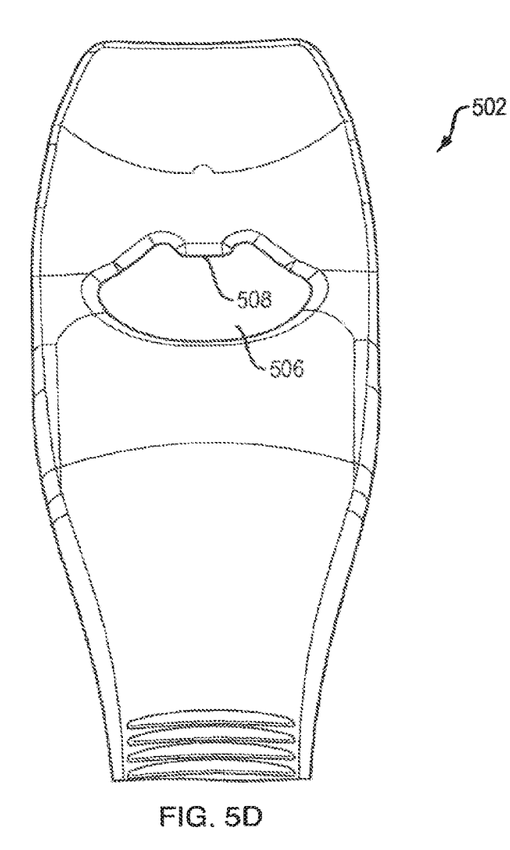

In some embodiments, pocket-sizing and marking functionalities are not integrated into the same device, but instead are provided by two separate surgical instruments, each including a handle portion and, fixedly attached to the handle, the replica or marking portion. FIG. 5A illustrates a stand-alone marking instrument (or "marker") 500, and FIGS. 5B-5D provide close-up views of the marking portion 502 from different perspectives. The marking portion 502 may be shaped to follow the contours of the relevant anatomy so as to prevent causing damage to delicate tissue; for the illustrated embodiment, the anatomical organ is the eye. Further, the marking portion 502 may be angled relative to the handle 504, as shown, to promote ease of use in the tool's surgical environment by allowing the marker 500 to easily navigate a crowded operating area without interfering with other surgical tools. The marker 500 may have a distinctly shaped cut-out 506 with an edge 508 intended for alignment with the eye's limbus 314. On its underside 510, the marking portion may have one or more non-piercing protrusions 512 that serve as marking tips. Once the marker 500 is properly aligned, the surgeon may apply pressure to the marking portion 502, causing the marking tips 512, in turn, to apply pressure to specific locations of the eye to thereby label the prospective placement sites of the pars plana clip 312 and cannula 310. The marking tips 512 leave temporary pressure marks on the eye that may be marked either immediately afterwards with a different tool (e.g., a felt-tip pen) or simultaneously if the marking tips are coated with surgical ink (e.g., FDA-approved Gentian Violet Ink, or any prep-resistant and/or waterproof permanent, as used in medical markers provided by, e.g., Viscot Medical, LLC, New Jersey).

The handle portion 504 of the marking instrument 500 may be rod-shaped and, optionally, include a textured gripping area 514, as shown in FIG. 5A. Alternatively, it may take the shape of any of the handle portions described above with regard to FIGS. 1 and 2A-2C, or any other suitable shape.

Surgical sizers and markers as described herein may be constructed using injection molding, machining, stereolithography, or other 3D manufacturing procedures known to persons of skill in the art. The construction of the surgical instrument may be straightforwardly adapted to its intended application and use. For example, a surgical sizer or marker intended for repeated use may be made of an autoclave-compatible material (i.e., a material that withstands the high-pressure, high-temperature steam used in an autoclave to sterilize the tool), such as metal (e.g., stainless steel, titanium, niobium, nickel titanium ("nitinol"), or an alloy of comparable properties) or certain polymer materials (e.g., polyether ether ketone or polypropylene). On the other hand, an instrument intended for one-time use may be manufactured from a disposable polymer material, preferably one that degrades during autoclaving to ensure that the instrument is not used more than once (such as, e.g., caprolactone, lactic acid, glycolic acid, acrylic, polycarbonate, or acrylonitrile butadiene styrene). In various embodiments, the surgical sizer, or its surface, is made of a biocompatible material, such as a biocompatibel metal (e.g., titanium or titanium alloys, colbalt-chrome alloys, molybdenum or molybdenum alloys, nitonol (a titanium-nickel alloy), certain types of stainless steel, gold, platinum, nickel alloys, or alumina ceramics) or polymer (e.g., polyether ether ketone, polypropylene, urethane, teflon, polyethylene, polymethylmethacrylate, certain epoxies, silicone, or parylene).

The external surfaces of the surgical sizer or marker are preferably non-abrasive and/or finished with smooth edges in order to prevent damage to the surrounding tissues contacted during implantation. In some embodiments, the surgical instrument is surface-coated with parylene or a comparable hydrophobic material for an optimized smooth surface; surface coatings may be applied to both metal and disposable plastic tools. In one preferred embodiment, the instrument is injected-molded out of polymer (SOMOS 11122) and then coated with Parylene C. Additionally, the underside of the instrument may be dipped in silicone or other materials commonly used by those skilled in the field to further optimize the surface. During the coating procedure, the groove, holes, or indentations in the distal portion of the handle or the marking portion may be used to hold the instrument so as to minimize the surface area that is not coated with conventional coating procedures.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. In particular, embodiments of the invention need not include all of the features nor have all of the advantages described herein. Rather, they may possess any subset or combination of features and advantages. Accordingly, the described embodiments are to be considered in all respects as only illustrative and not restrictive.

What is claimed is:

1. A kit enabling surgical implantation of an implantable device, the kit comprising:
    an implantable ophthalmic drug pump adapted for implantation between rectus muscles of an eye, the pump comprising (i) a pump housing, (ii) two or more suture anchors for receiving sutures configured to fasten the pump to underlying sclera of the eye, and (iii) a cannula extending from the housing and terminating at an end configured to be insertable into the eye;
    a marking instrument comprising:
        a marking portion; and
        a grippable handle portion extending away from and joined to the marking portion, the grippable handle portion having a length adequate to facilitate external manual retention of the marking instrument when the marking portion is in use and disposed on the eye, wherein (i) the marking portion has a top surface and an underside surface opposed to the top surface, the underside surface being configured to face the eye when the marking instrument is in use, (ii) the marking portion is angled relative to the handle portion and is shaped to follow contours of the eye, and (iii) the underside surface includes one or more non-piercing protrusions configured for marking the eye, to label placement sites on the eye for two or more sutures and a point of insertion of the cannula into the eye, responsively to application of pressure thereto via the grippable handle portion; and
    for use with the marking instrument, a sizing instrument comprising (i) a handle portion and (ii) a pocket-forming portion extending from the handle portion, wherein the pocket-forming portion comprises a replica of the implantable drug pump.

2. The kit of claim 1, wherein the marking instrument is biocompatible and comprises at least one of a polymer material or a metal.

3. The kit of claim 1, wherein the marking instrument comprises stainless steel, titanium, niobium, nickel titanium, or an alloy.

4. The kit of claim 1, wherein the marking instrument comprises a metal that is autoclave-safe.

5. The kit of claim 1, wherein the marking instrument comprises a polymer that is autoclave-degradable.

6. The kit of claim 1, wherein the replica is positively scaled.

7. The kit of claim 1, further comprising a parylene coating on a surface portion of the marking instrument.

8. The kit of claim 1, wherein the handle portion of the marking instrument is planar.

9. The kit of claim 1, wherein the handle portion of the marking instrument is non-planar.

10. The kit of claim 1, wherein the handle portion of the marking instrument comprises at least one marking in a distal portion of the handle.

11. The kit of claim 1, wherein the handle portion of the marking instrument comprises, at an end opposite the marking portion, a cut-out that is anatomically compatible with a human thumb.

12. The kit of claim 11, wherein the cut-out is textured.

13. The kit of claim 11, wherein the cut-out forms a circle, a slot, or a hook shape.

14. The kit of claim 1, wherein at least a portion of the marking portion is joined to the handle portion in a planar fashion.

15. The kit of claim 1, wherein the marking portion includes a fully enclosed cut-out region therethrough, the cut-out region including an internal straight edge for alignment with a limbus of the eye.

16. The kit of claim 15, wherein (i) the marking portion comprises (a) a proximal section substantially parallel to and extending from the handle portion and (b) a distal section including the one or more non-piercing protrusions, the distal section extending away from the proximal section at a non-zero angle thereto, and (ii) the fully enclosed cut-out region extends from within the proximal section into the distal section.

17. The kit of claim 15, wherein the internal straight edge of the fully enclosed cut-out region is substantially perpendicular to a side surface of the handle portion.

18. The kit of claim 15, wherein the internal straight edge of the fully enclosed cut-out region is substantially parallel to a front surface of the marking portion, the front surface of the marking portion spanning the top and underside surfaces of the marking portion.

19. The kit of claim 1, wherein the non-piercing protrusions are coated with surgical ink.

20. The kit of claim 1, wherein the grippable handle portion is joined to the marking portion on a surface thereof spanning the top and underside surfaces.

21. The kit of claim 1, wherein, at a seamless interface between the grippable handle portion and the marking portion, a cross-section of the handle portion is equal in size to a cross-section of the marking portion.

22. The kit of claim 21, wherein a width of the handle portion increases in a direction toward the marking portion.

23. The kit of claim 1, wherein the cannula terminates at a pars plana clip, the pars plana clip defining therethrough two or more openings for receiving sutures.

24. A method of surgical implantation of an implantable drug pump, the method comprising:
providing a kit comprising:
an implantable ophthalmic drug pump adapted for implantation between rectus muscles of an eye, the pump comprising (i) a pump housing, (ii) two or more suture anchors for receiving sutures configured to fasten the pump to underlying sclera of the eye, and (iii) a cannula extending from the housing and terminating at an end configured to be insertable into the eye;
a marking instrument comprising:
a marking portion; and
a grippable handle portion extending away from and joined to the marking portion, the grippable handle portion having a length adequate to facilitate external manual retention of the marking instrument when the marking portion is in use and disposed on the eye, wherein (i) the marking portion has a top surface and an underside surface opposed to the top surface, the underside surface being configured to face the eye when the marking instrument is in use, (ii) the marking portion is angled relative to the handle portion and is shaped to follow contours of the eye, and (iii) the underside surface includes one or more non-piercing protrusions configured for marking the eye, to label placement sites on the eye for two or more sutures and a point of insertion of the cannula into the eye, responsively to application of pressure thereto via the grippable handle portion; and
for use with the marking instrument, a sizing instrument comprising (i) a handle portion and (ii) a pocket-forming portion extending from the handle portion, wherein the pocket-forming portion comprises a replica of the implantable drug pump;
aligning an internal edge of a cut-out defined in the marking instrument with a limbus of an eye;
thereafter, applying pressure to the marking portion of the marking instrument, thereby causing the one or more non-piercing protrusions on the underside of the marking portion to label placement sites on the eye of two or more anchoring sutures and a point of insertion, in the eye, of the cannula of the drug pump;
implanting the drug pump between rectus muscles of the eye;
fastening the drug pump to underlying sclera of the eye, at the labeled placement sites, with two or more permanent sutures each extending through one of the suture anchors on the drug pump; and
inserting the cannula of the drug pump into the eye at the labeled point of insertion.

25. The method of claim 24, further comprising placing donor tissue over the cannula.

26. The method of claim 25, wherein the donor tissue comprises sclera tissue or pericardium tissue.

27. The method of claim 24, wherein the point of insertion is on a pars plana of the eye.

28. The method of claim 24, wherein the cannula terminates at a pars plana clip, further comprising suturing the pars plana clip to the eye.

* * * * *